United States Patent
Lin et al.

(10) Patent No.: US 7,971,916 B2
(45) Date of Patent: Jul. 5, 2011

(54) RECONFIGURABLE ROBOTIC END-EFFECTORS FOR MATERIAL HANDLING

(75) Inventors: Yhu-Tin Lin, Rochester Hills, MI (US); James W. Wells, Rochester Hills, MI (US); Roland J. Menassa, Macomb, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 375 days.

(21) Appl. No.: 12/125,676

(22) Filed: May 22, 2008

(65) Prior Publication Data
US 2009/0292298 A1 Nov. 26, 2009

(51) Int. Cl.
*A47B 97/00* (2006.01)
(52) U.S. Cl. ................. 294/65; 269/24; 269/27
(58) Field of Classification Search ........... 294/65; 414/752.1; 70/174; 606/130; 403/321, 122; 248/288.31, 288.51, 181.1, 481, 483; 269/24, 269/25, 27, 32
See application file for complete search history.

(56) References Cited

U.S. PATENT DOCUMENTS

| | | | | |
|---|---|---|---|---|
| 4,345,658 A * | 8/1982 | Danel et al. | ................. | 180/8.5 |
| 5,387,068 A * | 2/1995 | Pearson | ................. | 414/404 |
| 6,305,728 B1 * | 10/2001 | Holter et al. | ................. | 294/3 |
| 6,502,877 B2 * | 1/2003 | Schick et al. | ................. | 294/65 |
| 7,100,955 B2 * | 9/2006 | Nakamura | ................. | 294/65 |
| 2008/0281336 A1 * | 11/2008 | Zergiebel | ................. | 606/142 |

* cited by examiner

Primary Examiner — Saúl J Rodríguez
Assistant Examiner — Stephen Vu
(74) Attorney, Agent, or Firm — John A. Miller; Miller IP Group, PLC (57) ABSTRACT

A tool module associated with an end-effector for a robot arm that includes both linear and rotational locking mechanisms providing movement in five degrees of freedom. The tool module includes an integrated locking assembly that includes a linear locking mechanism and a rotary locking mechanism that are simultaneously locked and unlocked. The linear locking mechanism locks to a rod and the rotary locking mechanism locks and unlocks a shaft that is rigidly coupled to a swing arm. An opposite end of the swing arm includes another linear locking mechanism that locks and unlocks a shaft supporting a vacuum cup at an opposite end. The vacuum cup is mounted to a ball joint on the shaft that allows the vacuum cup to pivot. By locking and unlocking the locking mechanisms of the tool module, the end-effector can be readily configured to grasp and hold various parts of different dimensions and shapes.

20 Claims, 11 Drawing Sheets

RECONFIGURABLE ROBOTIC END-EFFECTORS FOR MATERIAL HANDLING

BACKGROUND OF THE INVENTION

1. Field of the Invention

This invention relates generally to a tool module associated with an end-effector for a robot arm and, more particularly, to a tool module associated with an end-effector for a robot arm that includes both rotational and linear locking mechanisms providing motion in five degrees-of-freedom.

2. Discussion of the Related Art

Manufacturing and assembly facilities typically employ robots having robotic arms that perform a variety of operations, such as welding parts, moving parts from one location to another location, installing parts, painting parts, etc. The robotic arm needs some device or devices that allow it to easily grasp the particular part for the particular operation. These devices are known in the art as end-effectors. An end-effector typically has a center boom and multiple rods extending therefrom that support a plurality of vacuum cups that pick up and hold parts when a vacuum is applied. Generally, the end-effector is built manually with various modular components, so that each vacuum cup can engage the part at a specific position and orientation.

Currently, end-effectors that are employed in manufacturing environments are designed for a specific part or a limited number of parts. Therefore, when the robot is used for different tasks, one end-effector typically needs to replace another end-effector or the position of the vacuum cups need to be changed. Typically, it is a slow and tedious process to set up the end-effectors due to numerous tightening, loosening and adjustments of the various end-effector components. As a result, in production, a long rack of pre-built sub-assemblies, also referred to as spiders of the end-effectors, are stocked for different parts and operations. Thus, the end-effectors take up a significant amount of floor space, a significant amount of inventory, can be lost, etc.

SUMMARY OF THE INVENTION

In accordance with the teachings of the present invention, a tool module associated with an end-effector for a robot arm is disclosed that includes both linear and rotational locking mechanisms providing movement in five degrees of freedom. The tool module includes an integrated locking assembly that includes a linear locking mechanism and a rotary locking mechanism that are simultaneously locked and unlocked by, for example, pneumatic pressure. The linear locking mechanism locks to a rod of the end-effector and the rotary locking mechanism locks and unlocks a shaft that is rigidly coupled to a swing arm. An opposite end of the swing arm includes another linear locking mechanism that locks and unlocks a shaft supporting a vacuum cup at an opposite end. The vacuum cup is mounted to a ball joint on the shaft that allows the vacuum cup to pivot. By locking and unlocking the locking mechanisms of the tool module, the end-effector can be readily configured to grasp and hold various parts of different dimensions and shapes.

Additional features of the present invention will become apparent from the following description and appended claims, taken in conjunction with the accompanying drawings.

DETAILED DESCRIPTION OF THE EMBODIMENTS

The following discussion of the embodiments of the invention directed to an integrated locking assembly including a linear locking mechanism and a rotary locking mechanism is merely exemplary in nature, and is in no way intended to limit the invention or its applications or uses. Particularly, the integrated locking assembly of the invention has particular application for a tool module that is part of an end-effector associated with a robotic arm. However, as will be appreciated by those skilled in the art, the integrated locking assembly will have application for other uses.

Figure 1:
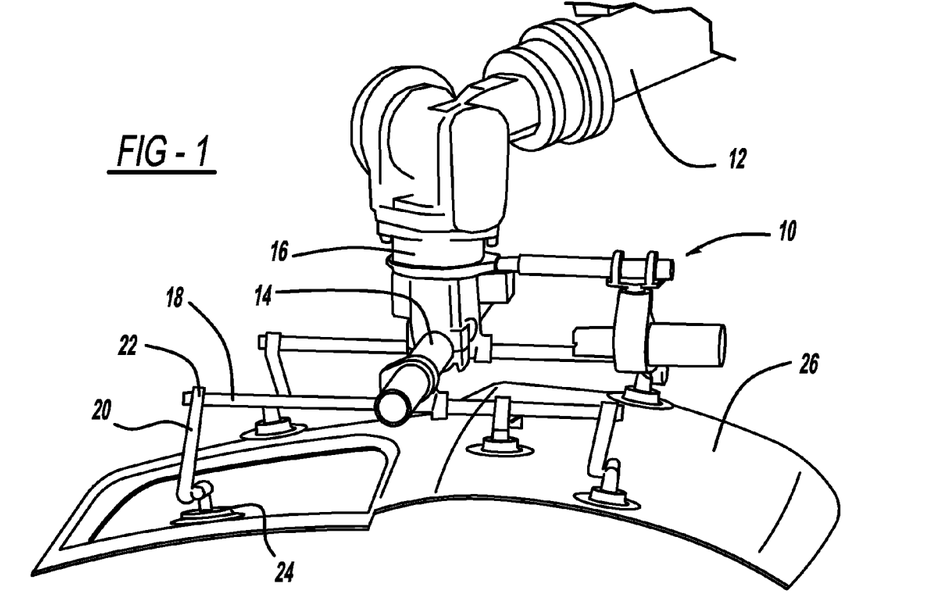
FIG. 1 is a perspective view of an end of a robot arm including an end-effector attached thereto where the end-effector is secured to a part.

FIG. 1 is a perspective view of an end-effector 10 mounted to a robot arm 12 of the type known in the art. The end-effector 10 includes a center boom 14 that is coupled to a coupling mechanism 16 at the end of the robot arm 12 in a manner that is well understood to those skilled in the art. The end-effector 10 includes a plurality of end-effector rods 18 secured to the boom 14, as shown. A plurality of tool modules 20 are positionable along the rod 18 and locked by conventional pinch clamps 22. An opposite end of the tool module 20 includes a suction or vacuum cup 24 that allows the end-effector 10 to be securely coupled to a part 26.

Figure 2:
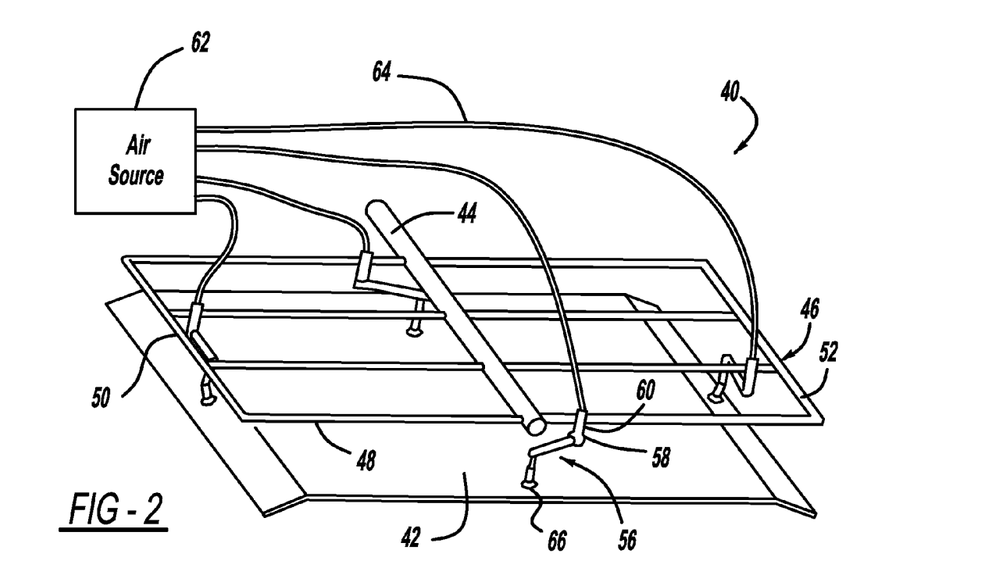
FIG. 2 is a perspective view of an end-effector including tool modules attached thereto, where the tool modules are secured to a part.

FIG. 2 is a perspective view of an end-effector 40 that can replace the end-effector 10, according to an embodiment of the present invention. As will be discussed in detail below, the end-effector 40 offers a number of advantages over those end-effectors known in the art that makes it more versatile so that one type of end-effector can be suitably coupled to many different types of parts, such as part 42. The end-effector 40 includes a main beam 44 that can be coupled to the coupler 16 of the robot arm 12. The main beam 44 is part of an end-effector frame 46 that includes a plurality of cross rods 48 connected to opposing end bars 50 and 52. The end-effector 40 also includes a plurality of tool modules 56 having a plurality of joints 58 that allow the tool module 56 to be coupled to the rods 48 in various orientations. The tool module 56 includes a linear locking mechanism 60 through which the rod 48 extends so that the tool module 56 can be secured or locked at any location along the rod 48 on which it is mounted. The tool or locked at any location along the rod 48 on which it is mounted. The tool module 56 also includes a suction cup 66 that grasps the part 42. An air source 62 provides pneumatic air to the tool modules 56 on lines 64 locking and unlocking the locking mechanisms on the tool modules and providing suction for the suction cups 66.

Figure 3:
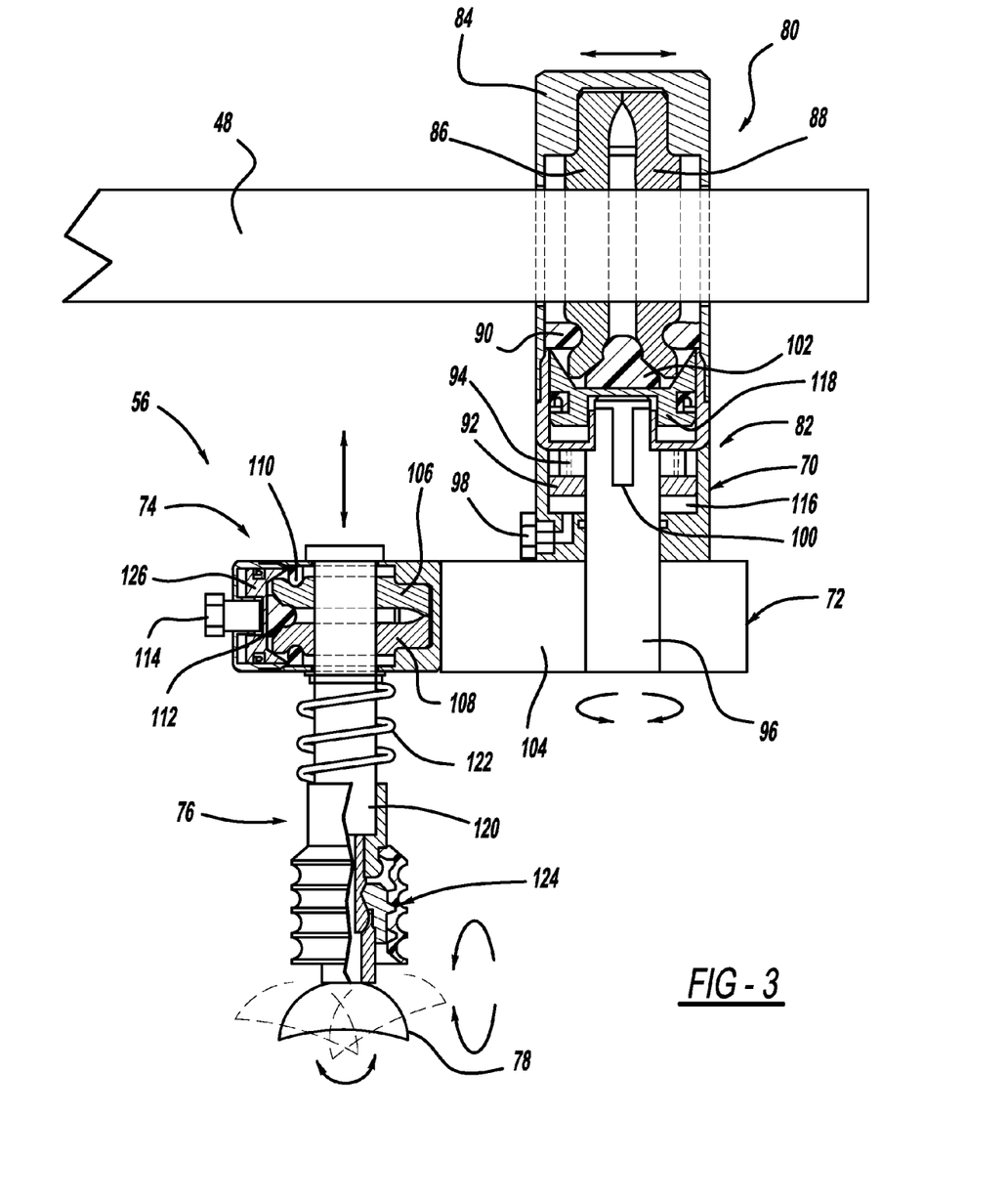
FIG. 3 is a cross-sectional view of one of the tool modules shown in FIG. 2.

FIG. 3 is a cross-sectional view of one of the tool modules 56 mounted to one of the cross rods 48. As will be discussed in detail below, the tool module 56 can be easily reconfigurable on the rod 48 with or without automation. The tool module 56 includes three major components, namely, an integrated linear and rotary locking assembly 70, a swing arm assembly 72 and a spring-loaded vacuum cup assembly 76 including a vacuum cup 78. When these three components are unlocked, a five degree-of-freedom reconfiguration of the vacuum cup 78 can be provided for any position and any orientation within the reach of the component design, as illustrated by the arrows.

The integrated linear and rotary locking assembly 70 includes a linear locking mechanism 80 and a rotary locking mechanism 82 mounted in a common housing 84. As will be discussed in detail below, the linear locking mechanism 80 includes opposing locking plates 86 and 88 that are pushed together by an annular spring element 90 that cause the plates 86 and 88 to be cocked relative to each other and lock onto the rod 48. The rotary locking mechanism 82 includes a locking plate 92 held in a locked position by a spring 94 that prevents a shaft 96 from rotating. When pneumatic air is provided to an inlet port 98, a pushing element 100 pushes against a piston 118 which pushes against a separating element 102 positioned between the locking plates 86 and 88 that causes the plates 86 and 88 to push against the bias of the spring element 90 and unbind the plates 86 and 88 so that they disengage from the rod 48 and are unlocked. Additionally, the pneumatic air provides pressure into a chamber 116 that pushes the plate 92 against the bias of the spring 94. As will be discussed in detail below, movement of the plate 92 unlocks the rotary locking mechanism 82 so that the shaft 96 can rotate.

The swing arm assembly 72 includes a swing arm 104 that is rigidly mounted to the shaft 96, such as by splines, so that when the shaft 96 rotates, the swing arm 104 also rotates. The swing arm assembly 72 also includes a linear locking mechanism 74 having opposing locking plates 106 and 108, an annular spring element 110, a piston 126 and a separating member 112, similar to the locking mechanism 80. An unlocking device 114, which can be manually or pneumatically controlled, is operable to cause the separating member 112 to separate and unlock the locking plates 106 and 108.

The vacuum cup assembly 76 includes a shaft 120 that is coupled to the linear locking mechanism 74. The shaft 120 is compression loaded by a spring 122 so that if the locking mechanism 74 is unlocked, the bias of the spring 122 causes the shaft 120 to drop and the cup 78 to go to its lowest position. The shaft 120 can be raised against the bias of the spring 122, and the mechanism 74 can be locked to hold the cup 78 at a range of Z positions. The assembly 76 also includes a universal or ball joint 124 linking the cup 78 to the spring-loaded shaft 120. The cup 78 is free to rotate on the ball joint 124 where there is no locking mechanism.

In operation, the linear locking mechanism 80 and the rotary locking mechanism 82 in the integrated locking assembly 70 can be unlocked with the push of a mechanical engagement or pneumatic actuation. The unlocked assembly 70 allows the swing arm assembly 72 to be located at a desired X-Y position by sliding and rotating the integrating locking assembly 70. The integrated locking assembly 70 is then locked by releasing the mechanical engagement or pneumatic actuation. The linear locking mechanism 74 on the swing arm assembly 72 is then unlocked mechanically or with compressed air. The vacuum cup 78 can then be pressed against a hard surface so that the shaft 120 moves upward through the locking mechanism 74 a sufficient distance in the Z direction so that the vacuum cup 78 will not touch a work piece in the programmed manipulation of the end-effector 40. Afterwards, the compressed air is discharged to lock the vacuum cup 78 at the raised Z position through the linear locking mechanism 74.

The end-effector 40 can be used for a multitude of different parts. Some parts will require a certain number of the tool modules 56 and other parts may require a different number of the tool modules 56. Those tool modules 56 that may not be need for a particular part remain attached to the end-effector 40, but unused. When the end-effector 40 is used to pick up a part, the linear locking mechanisms 74 for those vacuum cups 78 for those tool modules that are needed for the part are pneumatically unlocked, which restores those cups 78 to their lowered or fully extended Z position while leaving those unneeded cups locked at the raised non-touching position relative to the part. As the end-effector 40 begins touching the part, each unlocked vacuum cup 78 self adjusts in its own Z position and angular orientation to conform to the contour of the part.

As soon as all of the needed vacuum cups 78 are in full contact with the part, the compressed air is discharged again to lock the vacuum cups 78 in their individual Z positions. Lastly, the vacuum is activated on all the needed cups 78 to hold and move the part. Although the vacuum cups 78 seem to be able to float on the ball joint 124, each vacuum cup 78 is effectively locked by the solid work piece as long as at least three separated cups are in action. The different planes of cup rotation counter each other's movement. The end-effector 40 will, however, become unstable only when all of the vacuum cups are on the same line of the frame 46, which is rare and avoidable.

As discussed above, the tool module 56 includes a rotary lock mechanism. As will be discussed in detail below, the rotary locking mechanism associated with the tool module 56 can come in a variety of designs, some of which form part of the invention discussed herein.

Figure 4:
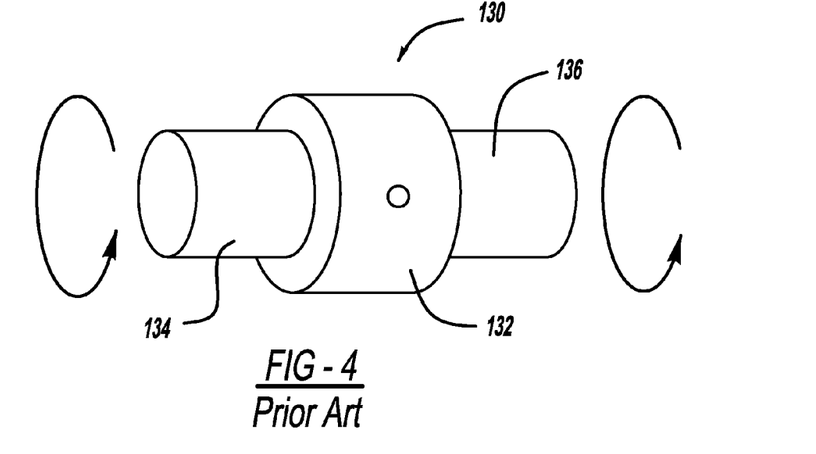
FIG. 4 is a perspective view of a bi-directional rotary locking clutch.

FIG. 4 is a perspective view of a rotary locking device or bi-directional clutch 130 of the type known in the prior art. The rotary locking device 130 includes a central housing 132 that encloses a locking mechanism of the device 130 discussed in detail below. An input shaft 134 is rotatably coupled to the locking mechanism within the housing 132 and an output shaft 136 is rotatably coupled to the locking mechanism within the housing 132. The locking device 130 operates such that the output shaft 136 is locked and prevented from rotating if the input shaft 134 is not rotated.

Figure 5:
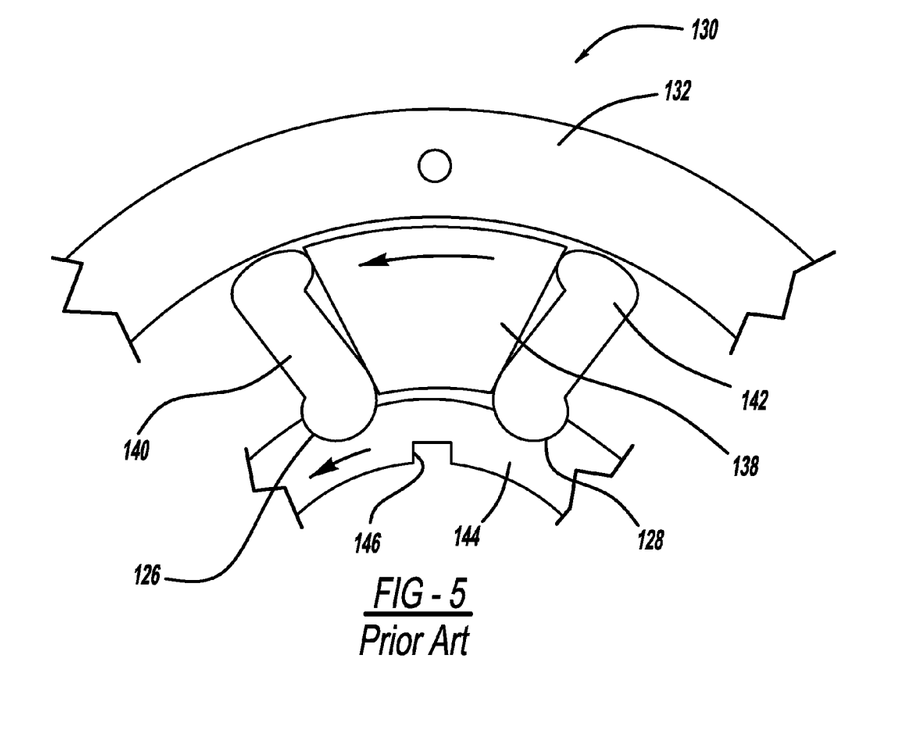
FIG. 5 is a broken-away, cross-sectional view of a sprag type bi-directional rotary locking clutch.

The locking device 130 can be a sprag type or a roller type device. FIG. 5 is a broken-away view of a portion of the device 130 showing part of the internal locking mechanism within the housing 132. The locking mechanism includes at least one control member 138 that is coupled to the input shaft 134, at least a set of sprag elements 140 and 142 positioned on either side of the control member 138 and an output ring 144 that positions the sprag elements 140 and 142 with hinged-like couplings 126 and 128. If the input shaft 134 and in turn the control element 138 are not rotated, then the sprag elements 140 and 142 are wedged to the housing 132 by a garter spring (not shown) that strings through the sprag elements 140 and 142 and prevents the output shaft 136 from rotating. If the input shaft 134 is rotated in the counter-clockwise direction, as shown, the control member 138 will disengage the sprag element 140 from the wedging position to the housing 132 and, simultaneously, drive the sprag element 140, and thus, the output ring 144 that is coupled to the output shaft 136 by a key and key slot 146, allowing the output shaft 136 to rotate in the counter-clockwise direction. The rotation, in the mean time, also drags the sprag element 142 away from its wedging position to the housing 132 and keeps the sprag element 142 free to move. Likewise, if the input shaft 134 is rotated in the clockwise direction, the control member 138 disengages the sprag element 142, which allows the ring 144 and the output shaft 136 to rotate in the clockwise direction.

Figure 6:
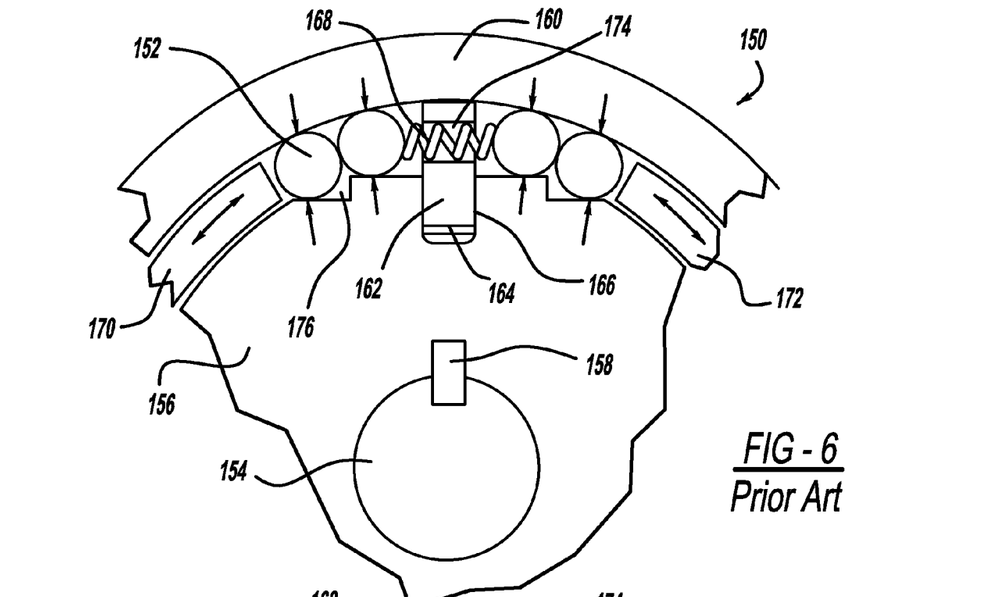
FIG. 6 is a broken-away cross-sectional view of a roller type bi-directional locking clutch.

FIG. 6 is a broken-away, cross-sectional view of another rotary locking device or bi-directional clutch 150 of the type known in the prior art that can replace the rotary locking device 130 and work under the same principle. The rotary locking device 150 is a roller type device that employs rollers 152 to lock and unlock an output shaft 154. The output shaft 154 is rigidly secured to a cam 156 by a key 158. A fixed housing 160 encloses the locking mechanism and at least one key 162 is coupled to the cam 156 through a corresponding key slot 166. A leaf spring 164 is provided in each slot 166 in the cam 156 in which the key 162 is positioned and keeps the key 162 floating with the movement of the rollers 152. A compression spring 168 extending through a bore 174 in each key 162 forces the rollers 152 on both sides of the key 162 to a position where they are wedged between the cam 156 and the housing 160, which prevents the cam 156 from rotating, and thus, the shaft 154 from rotating if input drive lugs 170 and 172 positioned adjacent to the rollers 152, as shown, are not moving. The input shaft (not shown) is coupled to the input lugs 170 and 172, and when the input shaft is rotated, the lugs 170 and 172 are pushed against the rollers 152 on one side of the key 162 and the bias of the springs 168 so that the rollers 152 are positioned into a wider area 176 between the cam 156 and the housing 160 where they are free to rotate. At the same time, the rollers 152 on the other side of the keys 162 are also dragged by the rotation to the wider area 176 on the other side of the keys 162 free of the wedging. By disengaging the rollers 152 in this manner, the cam 156 is decoupled from the housing 160, allowing the output shaft 154 to rotate.

Figure 7:
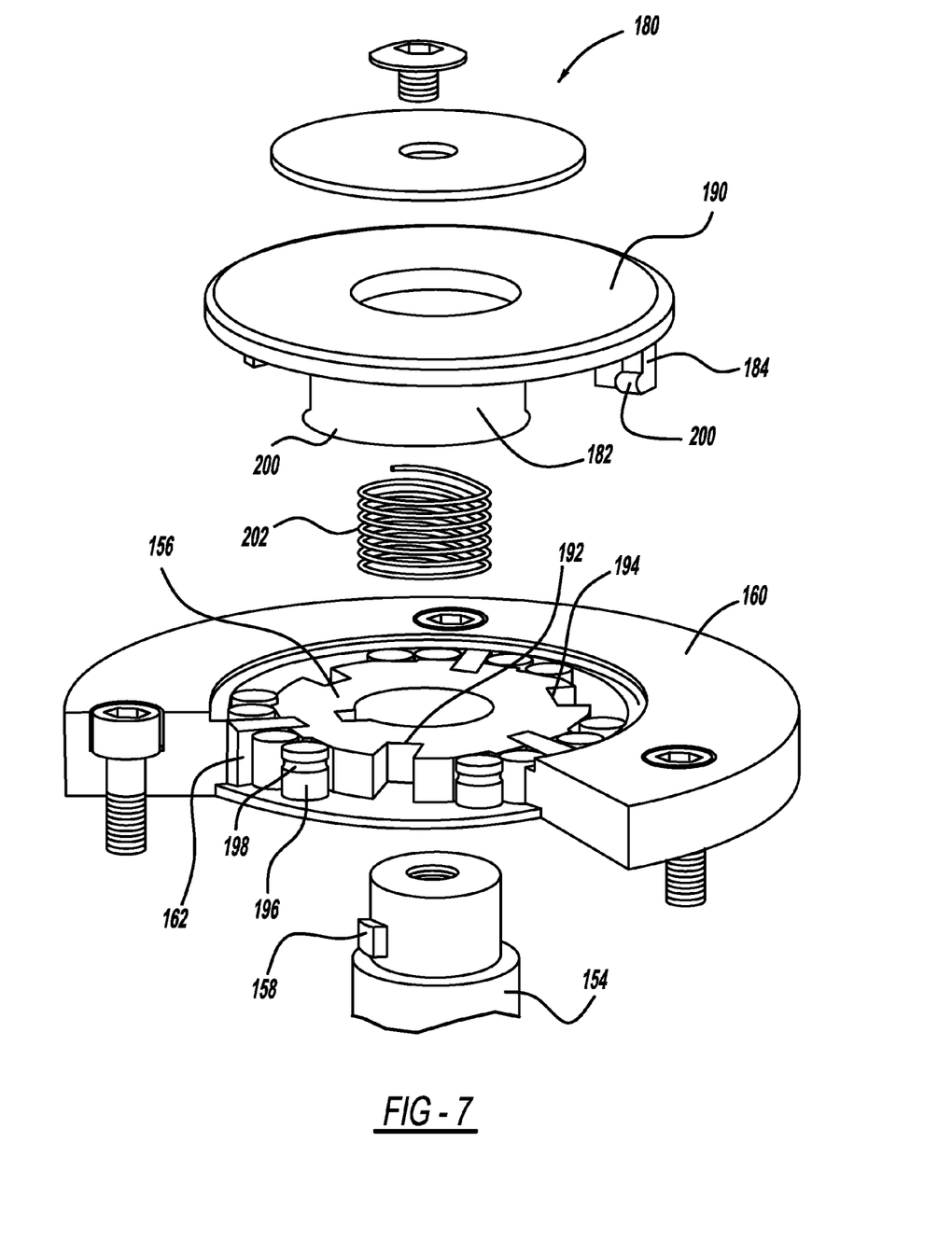
FIG. 7 is a broken-away, exploded perspective view of a rotary locking mechanism for the tool module shown in FIG. 3.
Figure 8:
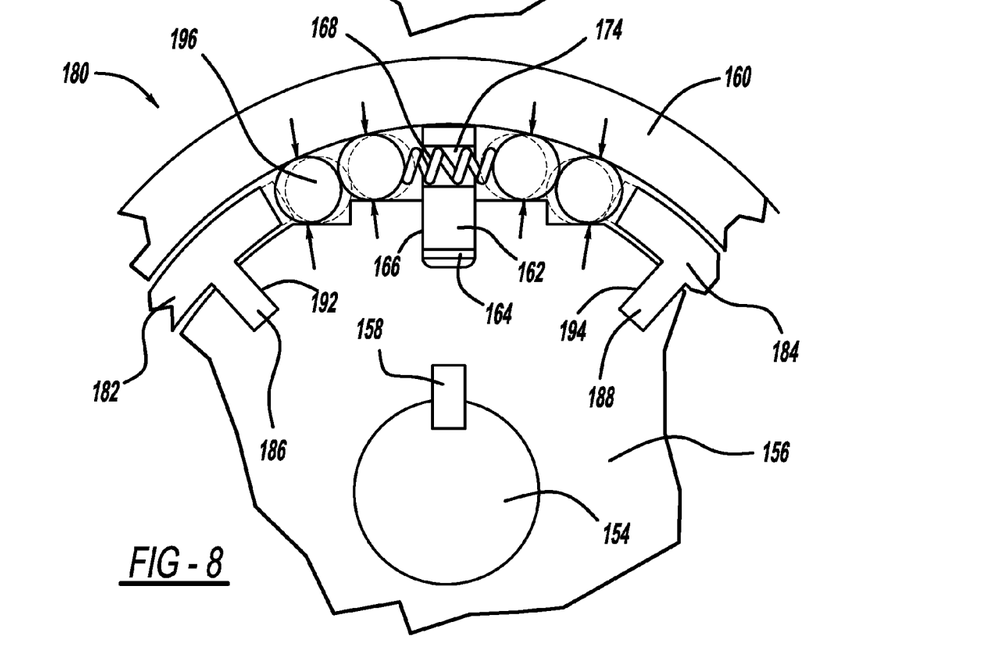
FIG. 8 is a broken-away, cross-sectional view of a portion of the locking mechanism shown in FIG. 7.
Figure 9:
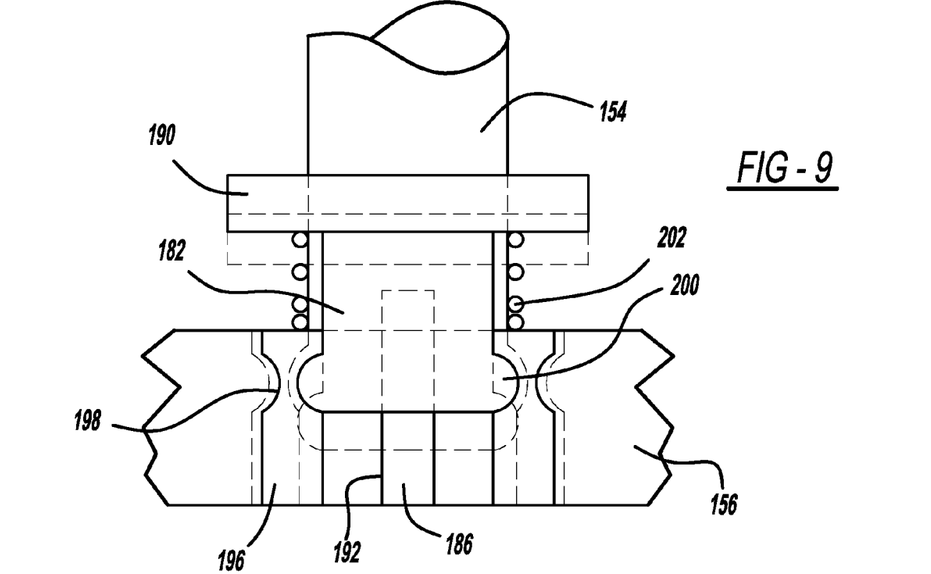
FIG. 9 is a broken-away, cross-sectional view of a portion of the locking mechanism shown in FIG. 7.

According to the invention, a rotary locking device is disclosed that operates on the principal of the locking device 150, but does not employ an input shaft to drive the rotation of the output shaft. FIG. 7 is an exploded perspective view of a rotary locking device 180 where common elements to the rotary locking device 150 are identified by the same reference number. FIG. 8 is a broken-away, cross-sectional view of the locking device 180 and FIG. 9 is another broken-away, cross-sectional view of the locking device 180. Solid lines show components of the locking device 180 in the locked position and dotted lines show components of the locking device 180 in the unlocked position.

In this embodiment, the input lugs 170 and 172 are replaced with T-shaped drive lugs 182 and 184. The T-shaped drive lugs 182 and 184 include lug keys 186 and 188, respectively, positioned in slots 192 and 194, respectively, in the cam 156. Further, the T-shaped lugs 182 and 184 include a rounded flange 200, as shown in FIG. 9. Also, the rollers 152 are replaced with rollers 196 that include indented neck portions 198 in which the flange 200 of the lugs 182 and 184 are positioned when the device 180 is in the locked position. Without any movement of the drive lugs 182 and 184, the cam 156 and the shaft 154 are locked to the stationary outer housing 160 by the wedging of the rollers 196. By pushing down on the plate 190 towards the cam 156 against the bias of a locking spring 202, the flange 200 is forced out of the neck portion 198, which causes the rollers 196 to move away from each other against the bias of the springs 168.

Each T-shaped lug 182 and 184 has a key slide-fit to the slots 192 and 194 of the cam 154 to keep its angular position, but allow them to move axially. The flange 200 of the T-shape lug 182 or 184 has a convex profile on both edges that mate with the neck portion 198 of the rollers 196 when the device 180 is in the locked position. There can be more than one lug where they are all connected by the top plate 190 that is concentric to the shaft 154. By pushing down on the top plate 190, the convex profile of the flange 200 will drive the rollers 196 apart, which in turn release the rollers 196 from the wedged position on both sides of the retaining key 162. The cam 156, the plate 190 and the shaft 154 are thus free to rotate as a whole unit. They will be locked again once the push load is removed, where the lugs 182 and 184 are positioned back in the neck portions 198 of the rollers 196 by the locking spring 202 exerting a bias on the top plate 190, and the rollers 196 are pushed to the wedging positions by the springs 168. The whole locking mechanism can be packaged in the housing 160 so that the top plate 190 can be actuated pneumatically, hydraulically or mechanically. For a smaller load capacity, the rollers 196 can be replaced with bearing balls. The flange 200 of the T-shaped lugs 182 and 184 can therefore be simplified to chamfers at the corners of the edges.

Figure 10:
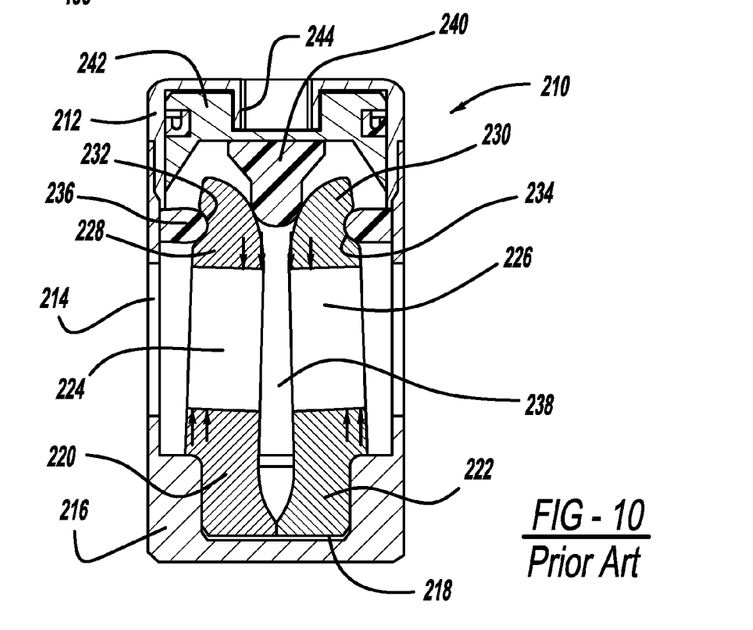
FIG. 10 is a cross-sectional view of a linear locking mechanism for the tool module shown in FIG. 3 in the locked position.
Figures 11, 12:
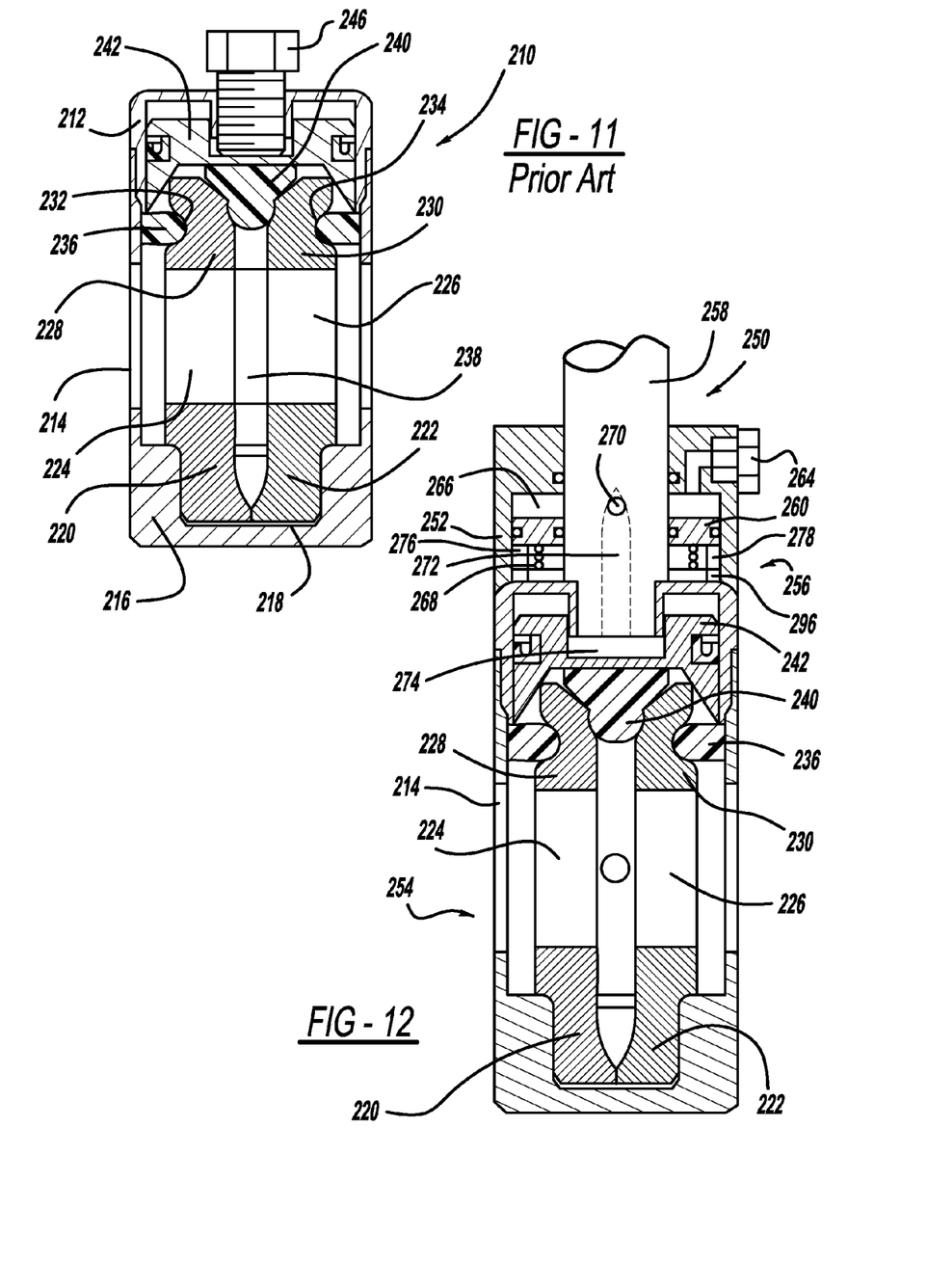
FIG. 11 is a cross-sectional view of the linear locking mechanism shown in FIG. 10 in the unlocked position.
FIG. 12 is a cross-sectional view of an integrated locking assembly with the linear locking mechanism in the unlocked position for the tool module shown in FIG. 3.

FIG. 10 is a cross-sectional view of a linear locking mechanism 210 of the type known in the art in a locked position and FIG. 11 is a cross-sectional view of the linear locking mechanism 210 in an unlocked position. The locking mechanism 210 includes an outer cylindrical housing 212 having a bore 214 extending sideways therethrough. A base portion 216 of the locking mechanism 210 includes a cylindrical opening 218 that accepts ends of opposing locking plates 220 and 222. The locking plates 220 and 222 include aligned bores 224 and 226, respectively, that align with the bore 214. An upper end 228 and 230 of the locking plates 220 and 222, respectively, include indentations 232 and 234, respectively, in which an annular spring member 236 is positioned. The configuration and position of the locking plates 220 and 222 define a gap 238 therebetween. A conical shaped separating member 240 is positioned between the ends 228 and 230 of the locking plates 220 and 222 in the gap 238, as shown, and is mounted to a piston 242 at a top portion of the housing 212. A threaded bore 244 exposes the piston 242. An actuation member 246 can be threaded into the bore 244 to force the piston 242 downward.

In FIG. 10, the actuating member 246 is removed from the opening 244 so that the piston 242 is free to move to a top portion of the housing 212, as shown. The spring bias provided by the annular spring member 236 pushes the ends 228 and 230 of the locking plates 220 and 222, respectively, together, which pushes on the separating member 240, thus pushing the piston 242 upward. This operation causes the ends of the plates 200 and 202 to pivot in the opening 218 so that the plates 210 and 222 are cocked relative to each other. This cocking effect narrows the gap 238 which causes a binding effect on a shaft that may extend through the bores 214, 224 and 246, holding the shaft in place.

When the actuating member 246 is threaded into the threaded bore 244, the piston 242 is forced downward against the bias of the spring 236, which causes the separating member 240 to be forced into the gap 238 between the ends 228 and 230 of the plates 220 and 222, respectively, to align the plates 220 and 222 so that the binding affect is removed. Thus, this unlocks the locking mechanism 210 from the shaft allowing it to slide through the bores 214, 224 and 226.

FIG. 12 is a cross-sectional view of an integrated locking assembly 250 that can be used as the assembly 70 where like elements to those discussed above are identified by the same reference number. The locking assembly 250 includes an outer housing 252 that houses a linear locking mechanism 254 and a rotary locking mechanism 256. The linear locking mechanism 254 operates in the same manner as the locking mechanism 210. The rotary locking mechanism 256 operates in the same manner as the rotary locking mechanism 180 discussed above, where a shaft 258 is the output shaft, and is rigidly secured to the swing arm 104, and where plate 260 is the top plate 190. The assembly 250 includes a pneumatic inlet 264 that accepts pressurized air. The pressurized air fills a chamber 266 that pushes on the plate 260 against the bias of a spring 268, which actuates T-shaped lugs 276 and 278 and rollers 296. The plate 260 moves against the bias of spring 268. A cross hole 270 is in fluid communication with the chamber 266 and delivers air pressure through channel 272 and chamber 274 that pushes on the piston 242. Thus, the rotary locking mechanism 256 and the linear locking mechanism 254 are simultaneously unlocked by application of the pneumatic pressure, which releases the tool module 56 from the shaft 48 and allows the swing arm 104 to swing.

Figures 13, 14:
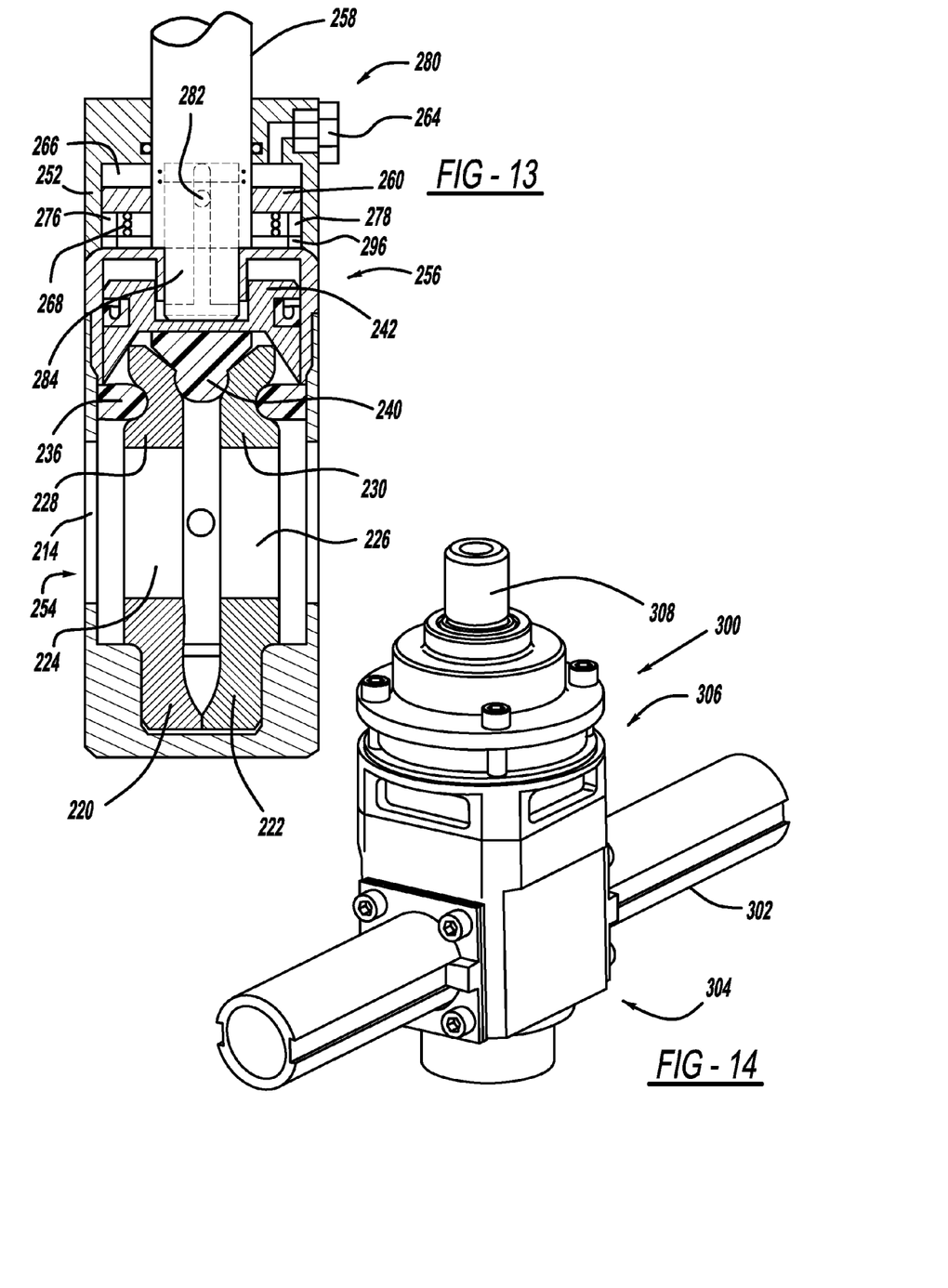
FIG. 13 is a cross-sectional view of an alternative integrated locking assembly with the linear locking mechanism in the unlocked position for the tool module shown in FIG. 3.
FIG. 14 is a perspective view of an integrated rotary and linear locking assembly for the tool module shown in FIG. 3.

FIG. 13 is a cross-sectional view of a locking assembly 280 similar to the locking assembly 250, where like elements are identified by the same reference numeral. In this design, the plate 260 and the lugs 276 and 278 are linked by a cross pin 282 to a plunger 284 inside the shaft 258. The plunger 284 is also connected to the piston 242. The air pressure will push the plunger 284 and the piston 242 down to unlock the end-effector rod from the locking plates 220 and 222. Meanwhile, the plunger 284 can drag the plate 260 along to release the rotary lock. Disengaging the air will allow the annular spring 236 to push in the locking plates 220 and 222, pushing the locking piston 242, the plunger 284 and in turn the plate 260 upward.

Figure 15:
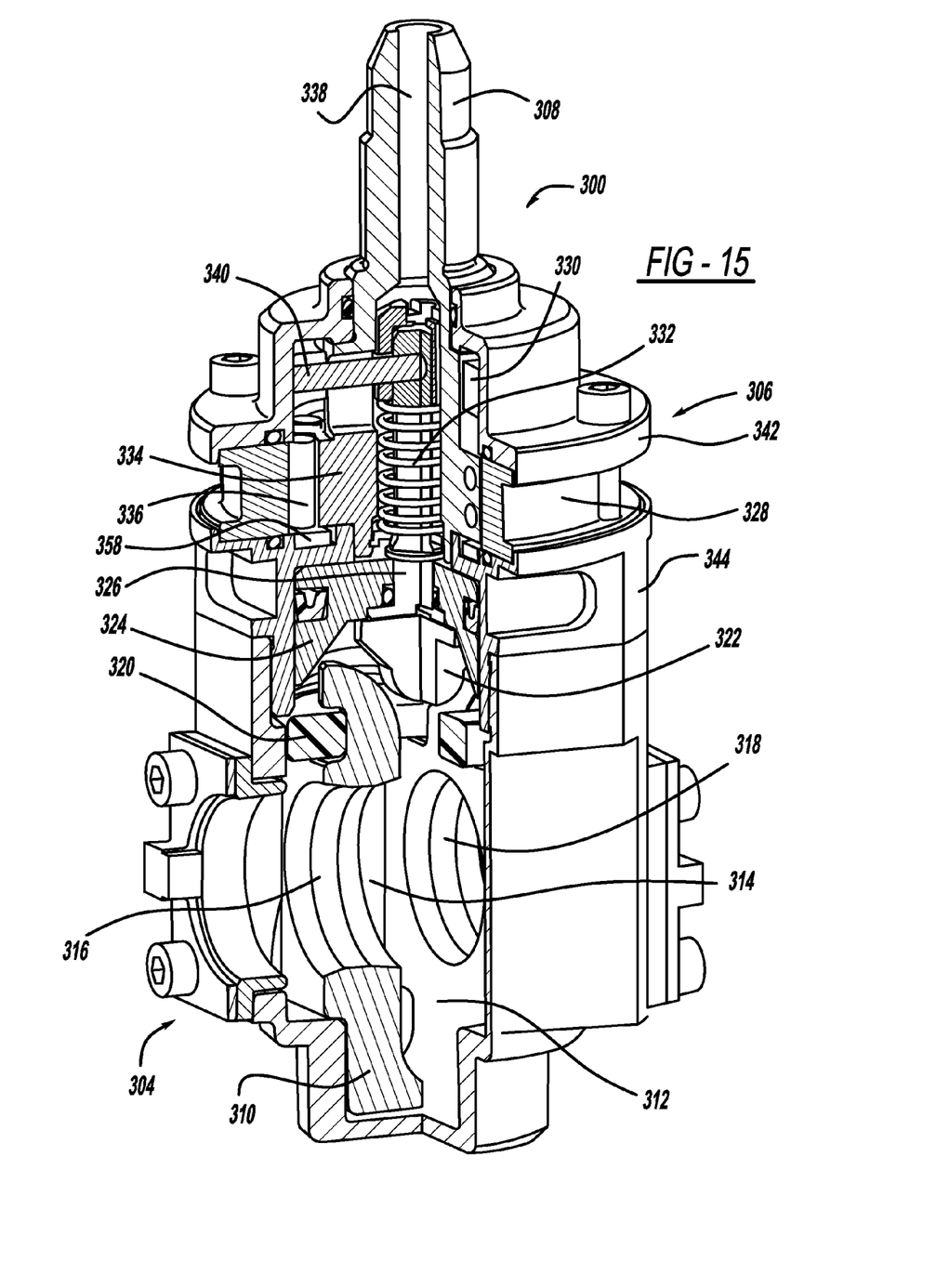
FIG. 15 is a partial cross-sectional view of the locking assembly shown in FIG. 14.
Figure 16:
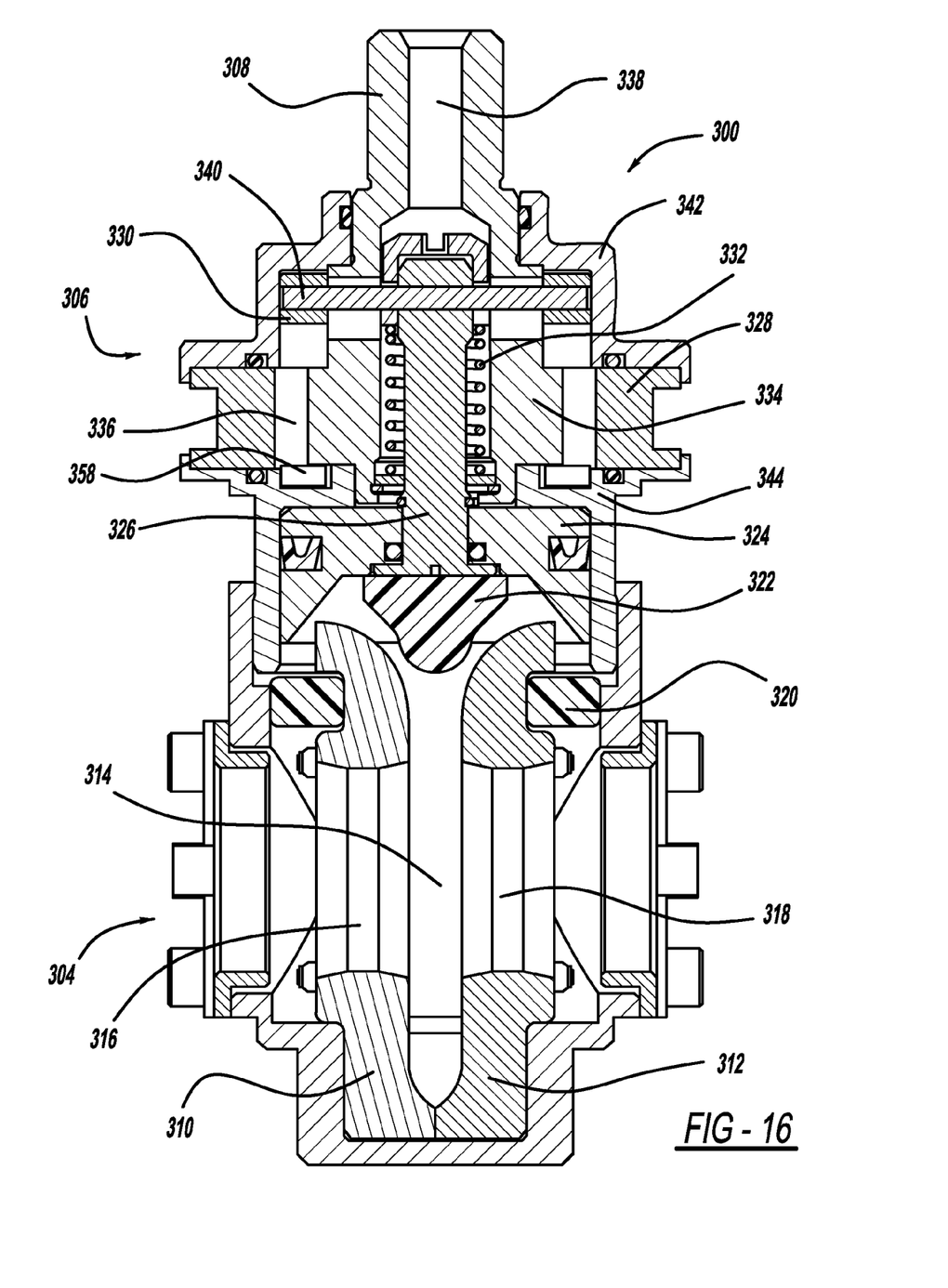
FIG. 16 is another cross-sectional view of the locking assembly shown in FIG. 14.
Figure 17:
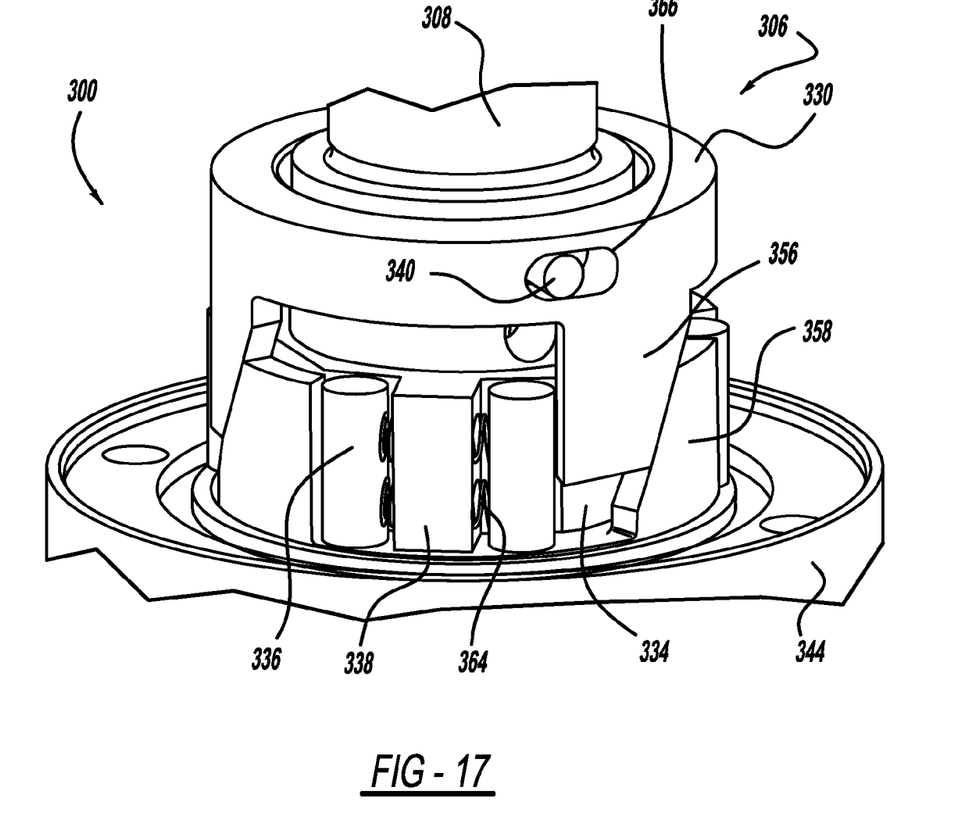
FIG. 17 is a broken-away perspective view of the rotary locking assembly shown in FIG. 14.

FIG. 14 is a perspective view of a locking assembly 300 mounted to a shaft 302 of an end-effector, such as the end-effector 40, according to another embodiment of the present invention. FIG. 15 is one cross-sectional view of the locking assembly 300, FIG. 16 is another cross-sectional view of the locking assembly 300 and FIG. 17 is a broken-away view of the locking assembly 300. The locking assembly 300 includes a linear locking mechanism 304 and a rotary locking mechanism 306 of the type discussed above. The linear locking mechanism 304 locks to the rod 302, and the rotary locking mechanism 306 locks an output shaft 308. The linear locking mechanism 304 includes opposing locking plates 310 and 312 defining a gap 314 therebetween, and including bores 316 and 318, respectively. An annular spring 320 pushes ends of the plates 310 and 312 together, as discussed above, and a separating member 322 separates the plates 310 and 312 against the bias of the spring 320 to unlock the linear locking mechanism 304. With pneumatic air pressure provided through a bore 338 in the shaft 308, a piston 324 is pushed down against the separating member 322 to provide the unlocking actuation.

The rotary locking mechanism 306 includes an actuation plate 330, a plurality of rollers 336, a cam 334 and a middle housing 328. Through a cross-pin 340 and an oblong plunger 326, the actuation plate 330 is coupled to the piston 324 such that the rotary locking mechanism 306 can be locked and unlocked at the same time as the linear locking mechanism 304. A helical compression spring 332 assists the annular spring 320 in returning both of the locking mechanisms 304 and 306 to the locking position. The middle housing 328, made from a heat treated wear resistant material, is sandwiched and bolted together with an upper housing 342 and a lower housing 344 to form the integrated locking assembly 300.

Instead of using the T-shaped drive lugs in this embodiment, the design of the rotary locking mechanism 306 includes opposing wedge members 356 and 358. The wedge member 356 is rigidly coupled to the actuation plate 330 and the wedge member 358 is free to rotate in the lower housing 344. When pressure is applied downward on the piston 324 and in turn the plate 330, an angled edge of the wedge member 356 rides along an angled edge of the wedge member 358, which pushes the wedge members 356 and 358 into the rollers 336 on both sides against the bias of springs 364, extending through key 338, so as to allow the cam 334 to rotate. When the pressure is released, the plate 330 is raised up with the piston 324 through the returning force of the helical spring 332 and the annular spring 320. The two angled wedge members 356 and 358 are thus separated, allowing the springs 364 to push the rollers 336 back into the locking position. A pair of oblong holes 366 in the plate 330 and around the ends of the cross-pin 340 provides the space for the wedge member 356 to rotate and push the rollers 336 on its side as the wedge member 358 does on the other side.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An end-effector operable to be coupled to a robot arm, said end-effector comprising:
a plurality of end-effector rods; and
a plurality of tool modules selectively coupled to the end-effector rods, each of the tool modules including an integrated locking assembly having a first linear locking mechanism and a rotary locking mechanism provided in a common housing, said first linear locking mechanism including opposing locking plates having aligned bores that lock to an end-effector rod, said rotary locking mechanism including an output shaft, said locking assembly being actuated to unlock the linear locking mechanism so that the tool module can slide along the end-effector rod and unlock the rotary locking mechanism to allow the output shaft to rotate where the first linear locking mechanism and the rotary locking mechanism are simultaneously locked and unlocked.

2. The end-effector according to claim 1 further comprising a swing arm rigidly mounted to the output shaft of the rotary locking mechanism.

3. The end-effector according to claim 2 further comprising a second linear locking mechanism mounted to the swing arm opposite to the output shaft, said tool module further including a vacuum cup shaft mounted to the second linear locking mechanism and a vacuum cup mounted to an end of the vacuum cup shaft opposite to the second linear locking mechanism where the vacuum cup can be raised and lowered using the second linear locking mechanism.

4. The end-effector according to claim 3 further comprising a ball joint mounted to the vacuum cup shaft opposite the second linear locking mechanism, said vacuum cup be mounted to the ball joint so that the combination of the first linear locking mechanism, the second linear locking mechanism, the rotary locking mechanism and the ball joint allow the tool module to have movement in five degrees of freedom.

5. The end-effector according to claim 1 wherein the rotary locking mechanism includes rollers positioned between the housing and a cam, said rollers being wedged between the housing and the cam to lock the rotary locking mechanism and being positioned in an open position between the housing and the cam to unlock the rotary locking mechanism.

6. The end-effector according to claim 5 wherein the rotary locking mechanism includes a plate and a plate spring, where the plate spring biases the plate to a locking position and pressure applied to the plate against the bias of the plate spring causes driving lugs to push the rollers to the open position to unlock the rotary locking mechanism.

7. The end-effector according to claim 6 wherein the driving lugs are T-shaped driving lugs each including a key portion that is slidably engaged in a slot in the cam, said rollers including an indented neck portion where an extended flange on a drive portion of the T-shaped lug is positioned within the indented neck portion of opposing rollers when the rotary locking mechanism is in the locked position and wherein sliding the key portion of the lug in the slot causes the extended flange to be forced out of the indented portion and cause opposing rollers to be pushed to the open position.

8. The end-effector according to claim 5 wherein the rotary locking mechanism includes a plate and a plate spring, where the plate spring biases the plate to a locking position and pressure applied to the plate against the bias of the plate spring causes a first angled wedge member to push against a second angled wedge member so that the first and second wedge members push against the rollers to push the rollers into the open position.

9. The end-effector according to 1 wherein the integrated locking assembly includes an opening that accepts a pneumatic air source, said pneumatic air source causing the first linear locking mechanism and the rotary locking mechanism to be unlocked.

10. The end-effector according to claim 1 wherein the plurality of end-effector rods include a main beam, a plurality of cross-rods and end rods coupled to the cross-rods to form a frame.

11. A tool module comprising:
an integrated locking assembly having a first linear locking mechanism and a rotary locking mechanism provided in a common housing, said first linear locking mechanism including opposing locking plates having aligned bores that can lock onto a rod, said rotary locking mechanism including an output shaft, said locking assembly being actuated to unlock the linear locking mechanism so that the tool module can slide along the rod and unlock the rotary locking mechanism to allow the output shaft to rotate where the first linear locking mechanism and the rotary locking mechanism are simultaneously locked and unlocked; and
a swing arm rigidly mounted to the output shaft of the rotary locking mechanism.

12. The tool module according to claim 11 further comprising a second linear locking mechanism mounted to the swing arm opposite to the output shaft, said tool module further comprising a vacuum cup shaft mounted to the second linear locking mechanism and a vacuum cup mounted to an end of the vacuum cup shaft opposite to the second linear locking mechanism where the vacuum cup can be raised and lowered using the second linear locking mechanism.

13. The tool module according to claim 12 further comprising a ball joint mounted to the vacuum cup shaft opposite the second linear locking mechanism, said vacuum cup be mounted to the ball joint so that the combination of the first linear locking mechanism, the second linear locking mechanism, the rotary locking mechanism and the ball joint allow the tool module to have movement in five degrees of freedom.

14. The tool module according to claim 11 wherein the rotary locking mechanism includes rollers positioned between the housing and a cam, said rollers being wedged between the housing and the cam to lock the rotary locking mechanism and being positioned in an open position between the housing and the cam to unlock the rotary locking mechanism.

15. The tool module according to claim 14 wherein the rotary locking mechanism includes a plate and a plate spring, where the plate spring biases the plate to a locking position and pressure applied to the plate against the bias of the plate spring causes driving lugs to push the rollers to the open position to unlock the rotary locking mechanism.

16. The tool module according to claim 15 wherein the driving lugs are T-shaped driving lugs each including a key portion that is slidably engaged in a slot in the cam, said rollers including an indented neck portion where an extended flange on a drive portion of the T-shaped lug is positioned within the indented neck portion of opposing rollers when the rotary locking mechanism is in the locked position and wherein sliding the key portion of the lug in the slot causes the extended flange to be forced out of the indented portion and cause opposing rollers to be pushed to the open position.

17. The tool module according to claim 14 wherein the rotary locking mechanism includes a plate and a plate spring, where the plate spring biases the plate to a locking position and pressure applied to the plate against the bias of the plate spring causes a first angled wedge member to push against a second angled wedge member so that the first and second wedge members push against the rollers to push the rollers into the open position.

18. The tool module according to 11 wherein the integrated locking assembly includes an opening that accepts a pneumatic air source, said pneumatic air source causing the first linear locking mechanism and the rotary locking mechanism to be unlocked.

19. A tool module that can be selectively coupled to an end-effector rod, said tool-module comprising:
an integrated locking assembly having a first linear locking mechanism and a rotary locking mechanism provided in a common housing, said first linear locking mechanism including opposing locking plates having aligned bores that can lock onto an end-effector rod, said rotary locking mechanism including an output shaft, said locking assembly being actuated to unlock the linear locking mechanism so that the tool module can slide along the end-effector rod and unlock the rotary locking mechanism to allow the output shaft to rotate where the first linear locking mechanism and the rotary locking mechanism are simultaneously locked and unlocked;
a swing arm assembly including a swing arm rigidly mounted to the output shaft of the rotary locking mechanism so that when the rotary locking mechanism is unlocked, the swing arm is able to rotate, said swing arm assembly further including a second linear locking mechanism mounted to the swing arm opposite to the output shaft; and a vacuum cup assembly including a vacuum cup shaft slightly mounted to the second linear locking mechanism and a vacuum cup mounted to an end of the vacuum cup shaft opposite to the second linear locking mechanism, said vacuum shaft assembly further including a ball joint mounted to the vacuum cup shaft opposite to the second linear locking mechanism, said vacuum cup being mounted to the ball joint so that the combination of the first linear locking mechanism, the second mechanism, the rotary locking mechanism and the ball joint allow the tool module to have movement in five degrees of freedom.

20. The tool module according to 19 wherein the integrated locking assembly includes an opening that accepts a pneumatic air source, said pneumatic air source causing the first linear locking mechanism and the rotary locking mechanism to be unlocked.

* * * * *